US008350186B2

(12) United States Patent
Jones et al.

(10) Patent No.: US 8,350,186 B2
(45) Date of Patent: Jan. 8, 2013

(54) LASER-PRODUCED IMPLANTS

(75) Inventors: Eric Jones, Limerick (IE); Christopher J. Sutcliffe, Liverpool (GB); Aiguo Wang, Wayne, NJ (US); Daniel E. Lawrynowicz, Cornwall, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1470 days.

(21) Appl. No.: 11/648,703

(22) Filed: Dec. 29, 2006

(65) Prior Publication Data

US 2008/0004709 A1    Jan. 3, 2008

Related U.S. Application Data

(60) Provisional application No. 60/755,260, filed on Dec. 30, 2005.

(51) Int. Cl.
*B23K 26/00* (2006.01)
(52) U.S. Cl. .......... 219/121.66; 219/121.65; 219/121.85
(58) Field of Classification Search ............. 219/121.66, 219/121.65, 121.85; 623/20.14, 20.17
See application file for complete search history.

(56) References Cited

U.S. PATENT DOCUMENTS

| | | |
|---|---|---|
| 3,605,123 A | 9/1971 | Hahn |
| 3,806,961 A | 4/1974 | Muller |
| 3,816,855 A | 6/1974 | Saleh |
| 4,085,466 A | 4/1978 | Goodfellow et al. |
| 4,164,794 A | 8/1979 | Spector et al. |
| 4,202,055 A | 5/1980 | Reiner et al. |
| 4,218,494 A | 8/1980 | Belmondo et al. |
| 4,305,340 A * | 12/1981 | Iwaki et al. ................ 72/379.4 |
| 4,344,193 A | 8/1982 | Kenny |
| 4,385,404 A | 5/1983 | Sully et al. |
| 4,502,161 A | 3/1985 | Wall |
| 4,636,219 A * | 1/1987 | Pratt et al. ................ 623/23.3 |
| 4,644,942 A | 2/1987 | Sump |
| 4,673,408 A | 6/1987 | Grobbelaar et al. |

(Continued)

FOREIGN PATENT DOCUMENTS

EP    1949989 A1    7/2008

(Continued)

OTHER PUBLICATIONS

R.H. Morgan, A.J. Papworth, C. Sutcliffe, P. Fox, W. O'Neill, "High density net shape components by direct laser re-melting of single phase powders," Journal of Materials Science, 37, (2002), pp. 3093-3100.

(Continued)

*Primary Examiner* — M. Alexandra Elve
(74) *Attorney, Agent, or Firm* — Lerner, David, Littenberg, Krumholz & Mentlik, LLP

(57) ABSTRACT

A method of producing an orthopedic implant including the steps of building a flat open model of at least a portion of an implant. The flat open model may be built using a selective laser sinter process. The flat open model preferably includes at least one groove along either a first surface or a second surface of the model. Next a force may be applied to the flat open model at predetermined locations to thereby cause the model to bend and assume a shape similar to a desired result. The now bent model may be resurfaced by either applying additional material such that the bent flat open model assumes the shape of a desired implant or the bent open model may be snap fit to an additional element.

11 Claims, 8 Drawing Sheets

U.S. PATENT DOCUMENTS

| | | | | |
|---|---|---|---|---|
| 4,714,473 | A * | 12/1987 | Bloebaum | 623/20.21 |
| 4,714,474 | A * | 12/1987 | Brooks, Jr. et al. | 623/20.33 |
| 4,719,908 | A | 1/1988 | Averill et al. | |
| 4,863,538 | A | 9/1989 | Deckard | |
| 4,944,817 | A | 7/1990 | Bourell et al. | |
| 4,961,154 | A | 10/1990 | Pomerantz et al. | |
| 4,969,907 | A | 11/1990 | Koch et al. | |
| 4,990,163 | A | 2/1991 | Ducheyne et al. | |
| 5,004,476 | A | 4/1991 | Cook | |
| 5,017,753 | A | 5/1991 | Deckard | |
| 5,031,120 | A | 7/1991 | Pomerantz et al. | |
| 5,034,186 | A | 7/1991 | Shimamune et al. | |
| 5,053,090 | A | 10/1991 | Beaman et al. | |
| 5,076,869 | A | 12/1991 | Bourell et al. | |
| 5,080,674 | A * | 1/1992 | Jacobs et al. | 623/20.17 |
| 5,108,432 | A * | 4/1992 | Gustavson | 623/23.54 |
| 5,147,402 | A | 9/1992 | Bohler et al. | |
| 5,155,324 | A | 10/1992 | Deckard et al. | |
| 5,158,574 | A | 10/1992 | Stone | |
| 5,171,282 | A * | 12/1992 | Pequignot | 623/20.35 |
| 5,176,710 | A | 1/1993 | Hahn et al. | |
| 5,192,328 | A | 3/1993 | Winters | |
| 5,219,362 | A | 6/1993 | Tuke et al. | |
| 5,282,861 | A | 2/1994 | Kaplan | |
| 5,282,870 | A | 2/1994 | Moser et al. | |
| 5,287,435 | A | 2/1994 | Cohen et al. | |
| 5,298,115 | A | 3/1994 | Leonard | |
| 5,314,478 | A | 5/1994 | Oka et al. | |
| 5,323,954 | A * | 6/1994 | Shetty et al. | 228/187 |
| 5,358,529 | A | 10/1994 | Davidson | |
| 5,368,602 | A | 11/1994 | de la Torre | |
| 5,386,500 | A | 1/1995 | Pomerantz et al. | |
| 5,398,193 | A | 3/1995 | deAngelis | |
| 5,443,510 | A | 8/1995 | Shetty et al. | |
| 5,443,518 | A | 8/1995 | Insall | |
| 5,490,962 | A | 2/1996 | Cima et al. | |
| 5,496,372 | A | 3/1996 | Hamamoto et al. | |
| 5,504,300 | A * | 4/1996 | Devanathan et al. | 219/121.64 |
| 5,514,183 | A | 5/1996 | Epstein et al. | |
| 5,549,700 | A | 8/1996 | Graham et al. | |
| 5,571,185 | A | 11/1996 | Schug et al. | |
| 5,571,196 | A | 11/1996 | Stein | |
| 5,609,646 | A | 3/1997 | Field et al. | |
| 5,616,294 | A | 4/1997 | Deckard | |
| 5,640,667 | A | 6/1997 | Freitag et al. | |
| 5,648,450 | A | 7/1997 | Dickens, Jr. et al. | |
| 5,681,354 | A | 10/1997 | Eckhoff | |
| 5,702,448 | A | 12/1997 | Buechel et al. | |
| 5,728,162 | A | 3/1998 | Eckhoff | |
| 5,735,903 | A | 4/1998 | Li et al. | |
| 5,773,789 | A * | 6/1998 | Devanathan et al. | 219/121.64 |
| 5,776,201 | A | 7/1998 | Colleran et al. | |
| 5,782,908 | A | 7/1998 | Cahalan et al. | |
| 5,795,353 | A | 8/1998 | Felt | |
| 5,824,098 | A | 10/1998 | Stein | |
| 5,824,102 | A | 10/1998 | Buscayret et al. | |
| 5,879,387 | A | 3/1999 | Jones et al. | |
| 5,879,398 | A | 3/1999 | Swarts et al. | |
| 5,928,285 | A | 7/1999 | Bigliani et al. | |
| 5,973,222 | A * | 10/1999 | Devanathan et al. | 623/11.11 |
| 5,989,472 | A | 11/1999 | Ashby et al. | |
| 6,046,426 | A | 4/2000 | Jeantette et al. | |
| 6,049,054 | A * | 4/2000 | Panchison et al. | 219/121.64 |
| 6,087,553 | A | 7/2000 | Cohen et al. | |
| 6,096,043 | A | 8/2000 | Techiera et al. | |
| 6,132,468 | A | 10/2000 | Mansmann | |
| 6,139,585 | A | 10/2000 | Li | |
| 6,190,407 | B1 | 2/2001 | Ogle et al. | |
| 6,206,924 | B1 | 3/2001 | Timm | |
| 6,206,927 | B1 | 3/2001 | Fell et al. | |
| 6,215,093 | B1 | 4/2001 | Meiners et al. | |
| 6,248,131 | B1 | 6/2001 | Felt et al. | |
| 6,251,143 | B1 | 6/2001 | Schwartz et al. | |
| 6,280,478 | B1 | 8/2001 | Richter et al. | |
| 6,283,997 | B1 | 9/2001 | Garg et al. | |
| 6,299,645 | B1 | 10/2001 | Ogden | |
| 6,355,086 | B2 | 3/2002 | Brown et al. | |
| 6,371,958 | B1 | 4/2002 | Overaker | |
| 6,395,327 | B1 | 5/2002 | Shetty | |
| 6,406,497 | B2 | 6/2002 | Takei et al. | |
| 6,454,811 | B1 | 9/2002 | Sherwood et al. | |
| 6,476,343 | B2 | 11/2002 | Keicher et al. | |
| 6,482,209 | B1 | 11/2002 | Engh et al. | |
| 6,494,914 | B2 | 12/2002 | Brown et al. | |
| 6,520,996 | B1 | 2/2003 | Manasas et al. | |
| 6,530,951 | B1 | 3/2003 | Bates et al. | |
| 6,551,608 | B2 | 4/2003 | Yao | |
| 6,558,421 | B1 | 5/2003 | Fell et al. | |
| 6,582,715 | B1 | 6/2003 | Barry et al. | |
| 6,599,301 | B2 | 7/2003 | Vibe-Hansen et al. | |
| 6,632,246 | B1 | 10/2003 | Simon et al. | |
| 6,652,246 | B1 | 11/2003 | Lin et al. | |
| 6,652,587 | B2 | 11/2003 | Felt et al. | |
| 6,682,567 | B1 | 1/2004 | Schroeder | |
| 6,686,437 | B2 | 2/2004 | Buchman et al. | |
| 6,699,252 | B2 | 3/2004 | Farr, II et al. | |
| 6,709,462 | B2 | 3/2004 | Hanssen | |
| 6,712,822 | B2 | 3/2004 | Re et al. | |
| 6,712,856 | B1 | 3/2004 | Carignan et al. | |
| 6,716,957 | B2 | 4/2004 | Tunc | |
| 6,770,099 | B2 | 8/2004 | Andriacchi et al. | |
| 6,846,329 | B2 | 1/2005 | McMinn | |
| 6,850,125 | B2 | 2/2005 | Norman et al. | |
| 6,855,165 | B2 | 2/2005 | Fell et al. | |
| 6,863,689 | B2 | 3/2005 | Ralph et al. | |
| 6,866,684 | B2 | 3/2005 | Fell et al. | |
| 6,893,463 | B2 | 5/2005 | Fell et al. | |
| 6,911,044 | B2 | 6/2005 | Fell et al. | |
| 6,916,341 | B2 | 7/2005 | Rolston | |
| 6,921,264 | B2 | 7/2005 | Mayer et al. | |
| 6,923,831 | B2 | 8/2005 | Fell et al. | |
| 6,932,610 | B2 | 8/2005 | Ono et al. | |
| 7,168,283 | B2 * | 1/2007 | Van Note et al. | 72/364 |
| 7,494,507 | B2 * | 2/2009 | Dixon et al. | 623/17.14 |
| 7,674,517 | B2 | 3/2010 | Ramsey et al. | |
| 2001/0014403 | A1 | 8/2001 | Brown et al. | |
| 2003/0069638 | A1 | 4/2003 | Barlow et al. | |
| 2004/0009228 | A1 | 1/2004 | Tormala et al. | |
| 2005/0079200 | A1 | 4/2005 | Rathenow et al. | |
| 2005/0123672 | A1 * | 6/2005 | Justin et al. | 427/2.26 |
| 2005/0170159 | A1 | 8/2005 | Ramsey et al. | |
| 2006/0045903 | A1 | 3/2006 | Kadiyala et al. | |
| 2007/0225390 | A1 | 9/2007 | Wang et al. | |
| 2008/0161927 | A1 | 7/2008 | Savage et al. | |
| 2009/0068245 | A1 | 3/2009 | Noble et al. | |
| 2009/0087605 | A1 | 4/2009 | Ramsey et al. | |

FOREIGN PATENT DOCUMENTS

| | | |
|---|---|---|
| WO | 9606881 A2 | 3/1996 |
| WO | 2007058160 A1 | 5/2007 |

OTHER PUBLICATIONS

Dr. Kerron Harvey, producer, Research Intelligence, The University of Liverpool, Issue 13, Jun. 2002.

H.J. Niu and I.T.H. Chang, "Selective Laser Sintering of Gas and Water Atomized High Speed Steel Powders," Scripta Materialia vol. 41, No. 1, (1999), pp. 25-30.

C.K. Chua et al. Development of a Tissue Engineering Scaffold Structure Library for Rapid Prototyping. Parts 1 and 2, International Journal of Advanced Manufacturing Technology, (2003) vol. 21, pp. 291-312.

Meiners W, Over C, Wissenbach K, Poprawe R., Direct generation of metal parts and tools by selective laser powder remelting (SLPR). Proceedings of SFF, Austin, Texas, Aug. 9-11, 1999.

PCT/US2008/008955 International Preliminary Report on Patentability mailed Feb. 4, 2010.

PCT/US2008/008955 International Search Report and Written Opinion mailed Dec. 2, 2008.

* cited by examiner

US 8,350,186 B2

LASER-PRODUCED IMPLANTS

CROSS-REFERENCE TO RELATED APPLICATIONS

This application claims the benefit of the filing date of U.S. Provisional Patent Application No. 60/755,260 filed Dec. 30, 2005, the disclosure of which is hereby incorporated herein by reference.

BACKGROUND OF THE INVENTION

The present invention relates to a method of making a three-dimensional structure utilizing a flat substrate.

In particular, this invention relates to a computer-aided laser apparatus or other suited high energy beam, which sequentially remelts a plurality of powder layers to build a porous layer in a layer-by-layer fashion. The porous layer may be attached to an implant that may be created using a similar method.

Currently, implants such as femoral implants are constructed using various dies and casting processes. This procedure can be extremely expensive and time consuming. In addition, each implant must be made separately and requires its own casting device, which is usually destroyed when removing the completed implant.

The present application is particularly directed toward a method of forming a porous and partially-porous metallic structure having a bearing surface as well as metallic structures that are simply designed to be implanted into a person during surgery.

The field of free-form fabrication has seen many important recent advances in the fabrication of articles directly from computer-controlled databases. These advances, many of which are in the field of rapid prototyping of articles such as prototype parts and mold dies, have greatly reduced the time and expense required to fabricate articles, particularly in contrast to conventional machining processes in which a block of material, such as a metal, is machined according to the engineering drawings. One example of a modern rapid prototyping technology is the selective laser sintering process practiced by systems available from 3D Systems, Valencia, Calif. According to this technology, articles are produced in a layer-wise fashion, from a laser-fusible powder that is dispensed one layer at a time. The powder is fused, remelted or sintered, by the application of laser energy that is directed in raster-scan fashion to portions of the powder layer corresponding to a cross-section of the article. After fusing of the powder on one particular layer, an additional layer of powder is dispensed, and the process repeated with fusion taking place between the current layer and the previously laid layers, until the article is complete.

The field of rapid prototyping of parts has, in recent years, made large improvements in broadening high strain, high density parts for use in the design and pilot production of many useful articles including metal parts. These advances have permitted the selective laser remelting and sintering process to now also be used in fabricating prototype tooling for injection molding, with expected tool life in excess of 10,000 mold cycles. The technologies have also been applied to the direct fabrication of articles, such as molds from metal powders without a binder. Examples of metal powder reportedly used in such direct fabrication include two-phase metal powders of the copper-tins, copper-solder (the solder being 700 lead and 30% tin), and bronze-nickel systems. The metal articles formed in these ways have been quite dense, for example, having densities of up to 70% to 80% of full density (prior to any infiltration). Prior applications of this technology have strived to increase the density of the metal structure formed by the melting or sintering process. The field of rapid prototyping of parts has focused on providing high strength, high density parts for use and design in production of many useful articles, including metal parts.

But while the field of rapid prototyping has focused on increasing density of such three-dimensional structures, the field has not focused its attention on reducing the density of three-dimensional structures or growing a porous surface with a denser surface. Consequently, applications where porous and partially-porous metallic structures, and more particularly metal porous structures with interconnective porosity, are advantageous for use, have been largely ignored.

In addition, many structures, especially in the medical arts, require two different surfaces, each adapted for their own purposes. Along this line, a structure may have a first surface which needs to be porous for tissue in-growth and a second surface which should be adapted to be a bearing surface. Further, the first surface or portion may include different layers having different gradients of porosity. For example, the first surface may include an outer region having a porosity of approximately 80%. As you move normal with regard to the first surface the porosity may alter such that the porosity is increased or in a preferred embodiment, the porosity decreases even until the porosity is almost zero. Of course, the present invention contemplates a situation where the porosity alters from position to position depending on the requirements of the device.

Although different techniques have tried to provide such a method and apparatus, still greater techniques are needed in this area.

SUMMARY OF THE INVENTION

The present invention is directed to an implant and a method of making the implant. The method of constructing the implant includes providing a flat open model of a portion of a desired implant. The flat open model may be created with the use of scanning processes and computer software.

For instance, a 3-D model may be inputted into a computer program and the model flattened. The flattened model may then be reproduced using a selective laser sintering or melting process. The replicated model may also include various grooves as well as other desired features.

Once the model is replicated, porous pads may be attached to the flat open model. In an alternate embodiment the porous pads may be constructed on the flat open model during the SLS process.

A force may then be applied to the flat open model thereby causing the model to bend into a desired shape. The bent model may then be treated with various methods to form a final product.

DETAILED DESCRIPTION

The present invention relates to a method of forming an implant to be positioned in vivo during surgery, especially an orthopedic implant that replaces a joint, such as a knee joint, hip joint or shoulder joint. Although the present invention will be described with reference to a femoral component, the exemplified element should in no way be perceived as a limiting feature.

As used herein, the following directional definitions apply. Anterior and posterior mean nearer the front or nearer the back of the body respectively. Thus, for the knee joint described herein, anterior refers to that portion of the knee that is nearer the front of the body, when the leg is in an extended position. Proximal and distal mean nearer to or further from the root of the structure, respectively. For instance, the distal femur is part of the knee joint further from the hip joint while the proximal femur is closer to the hip joint. Finally, the adjectives medial and lateral mean nearer the sagittal plane or further from the sagittal plane respectfully.

Figure 1:
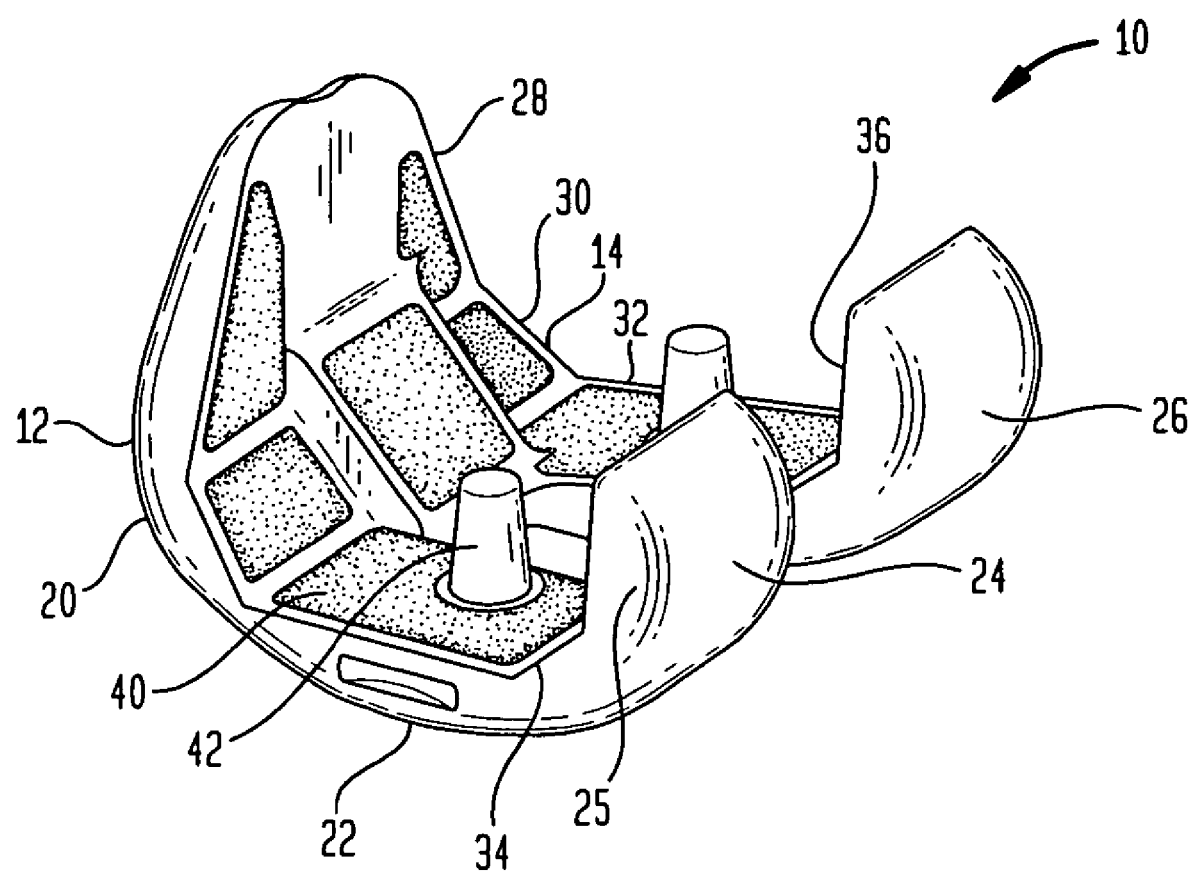
FIG. 1 is a perspective view of one embodiment of the present invention.

As shown in FIG. 1, a femoral component 10 generally includes an articulating external surface 12 and a bone contacting non-articulating internal surface 14. The external surface 12 generally includes an anterior surface 20, a distal surface 22 and a posterior surface 24. The posterior surface 24 is divided into a medial condylar surface 25 and a lateral condylar surface 26. The interior surface 14 may include an anterior wall 28, anterior chamfer 30, distal floor 32, posterior chamfer 34, and posterior wall 36, the posterior chamfer and posterior wall being shared by both condylar surfaces.

Femoral component 10 may comprise any biocompatible material having the mechanical properties necessary to function as a human knee femoral prosthesis. Preferably, femoral component 10 is comprised of titanium, titanium alloy, cobalt chrome alloy, stainless steel, or a ceramic. Particular compositions may be discussed herein depending on the method employed to construct the component and the particular requirements of the apparatus. Unless specifically stated, such compositions are merely illustrative.

The non-articulating internal surface 14 of the femoral component 10 is adapted to receive a resected distal femur (not shown in the figures). During the surgery, surgical cuts are made to the distal femur by any means, in any sequence and in any configuration known to those of skill in the art. In a preferred embodiment, the cuts of the resected distal femur correspond to the configuration of the internal surface 14 of the femoral component 10.

Along this line, the internal surface 14 may include a porous surface or as shown in FIG. 1, a plurality of porous pads 40 disposed along the internal surface at particular locations. The porous pads 40 abut the surface of the resected distal femur when the femoral component 10 is attached to the femur and preferably help to promote the growth of bone therein. As will be described below, the porous pads 40 may be integrally formed with the femoral component 10 or may separate elements that are first constructed and then attached to the femoral component. The internal surface 14 may also include pins 42 extending outwardly therefrom. The pins 42 are designed for anchoring the femoral component 10 to the femur. The pins 42 are not required in the femoral component 10.

Figure 2A:
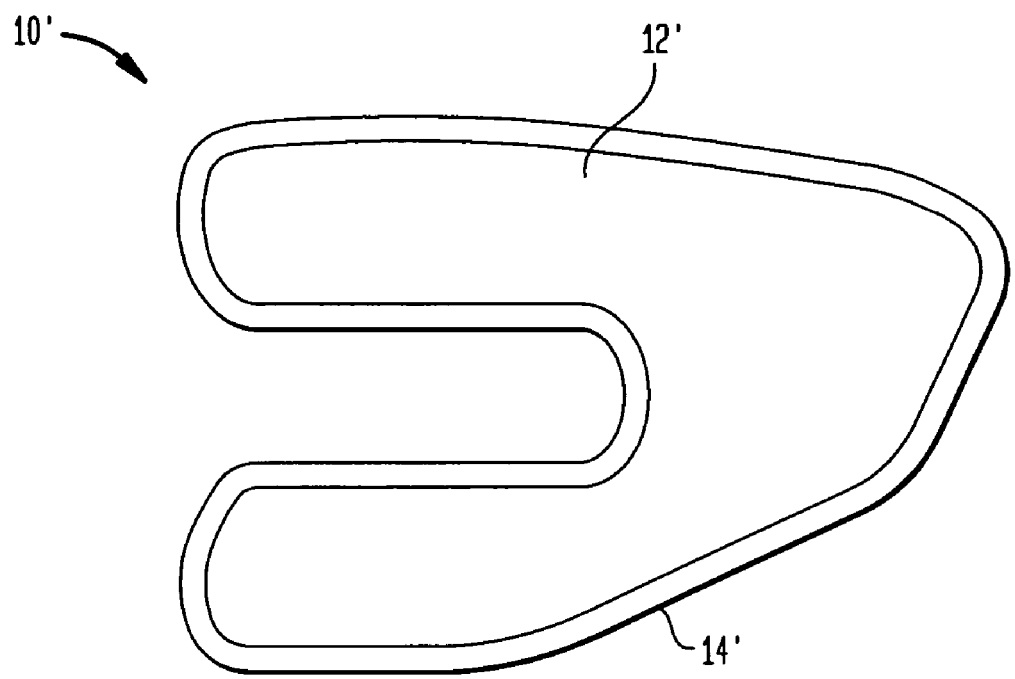
FIG. 2A is a top view of the embodiment of FIG. 1 at an early stage of an assembly process.
Figure 2B:
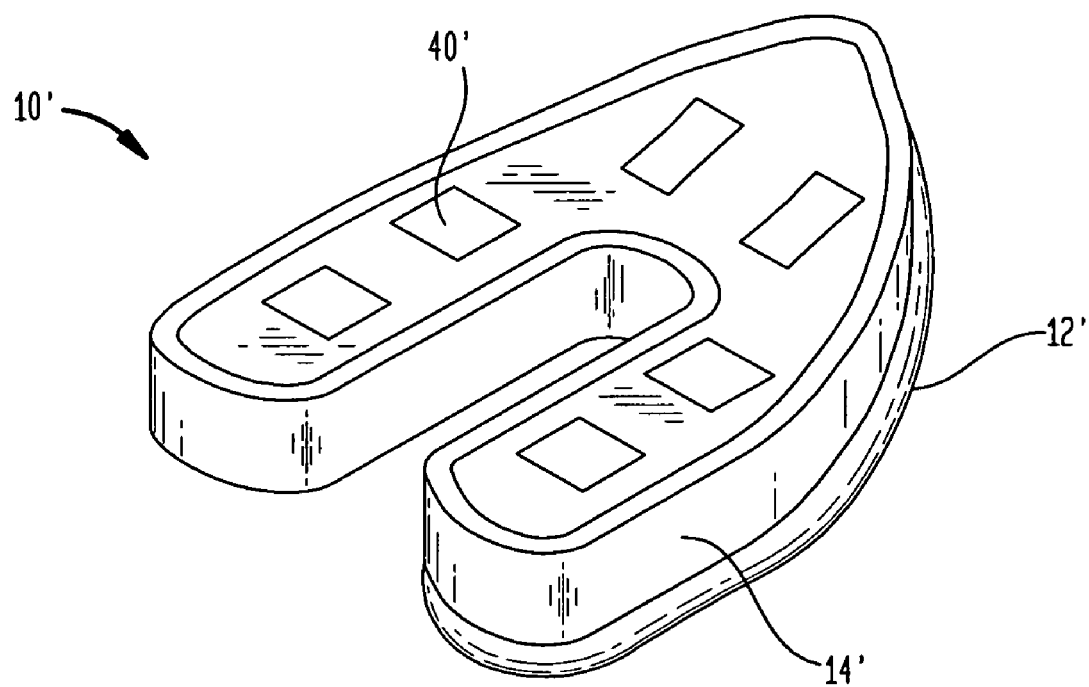
FIG. 2B is a side perspective view of the embodiment of FIG. 2A at a later stage of the assembly process.

In a method of constructing the femoral component 10, a profile of a femoral knee implant may be inputted into various types of computer software. The profile can then be modeled, manipulated and "opened" such that a planar embodiment of the femoral component is now stored in a computer, as illustrated by FIGS. 2A and 2B. The planar embodiment of the femoral component 10' is essentially a flattened and opened model of femoral component 10. Thus, the femoral component 10' also includes an articulating external surface 12' and a non-articulating internal surface 14', each surface including the same surfaces, chamfers and walls as before, with the various features being denoted by a (') so as to highlight the difference. Employing computer software, the femoral component 10' may be sliced into various layers simulating each layer of the component. Either the entire femoral component 10' or only a portion of the component may then be built using methods as described in commonly assigned U.S. patent Ser. Nos. 10/704,270 and 11/027,421, the disclosures of which are hereby incorporated herein by reference. In addition, U.S. patent application Ser. No. 11/295,008, entitled "Laser-Produced Porous Surface", filed on Dec. 6, 2005, is also hereby incorporated by reference herein.

In one such method of operation, the planar top side 50 of the femoral component 10' may be constructed using laser technology or any other high energy beam by employing a variety of scanning procedures. The planar top side 50 refers to the portion of the femoral component 10' that includes the non-articulating internal surface 14' and a certain depth therefrom and does not include the articulating external surface 12'. For instance, the top side of the femoral component 10' may be prepared by building a model onto a build platform using a layer-by-layer build process, each layer corresponding to a layer of the femoral component 10'. The structure may be prepared by populating the volume of the structure with a single unit repeating cell using proprietary software. The single unit cell may be an octahedron or any other symmetrical or even asymmetrical geometric shape. By varying the tessellation, size, construct and various other factors, each layer may be constructed with a particular porosity.

According to one method of forming a porous three-dimensional structure by laser melting, a powder of titanium, titanium alloys, stainless steel, cobalt chrome alloys, tantalum or niobium is disposed onto a substrate. The laser melting process includes scanning a laser beam onto the powder and in parallel scan lines with a beam overlap, e.g., scan spacing, followed by similar additional scans or subsequent scans at 90 degrees, by way of example. The type of scan chosen may depend on the initial layer thickness as well as the web height required. The web height refers to the height of a single stage of the femoral component 10'. The web height may be increased by depositing additional layers of powder of a structure and scanning the laser at the same angle of the previous scan. Further, the additional scan lines may be at any angle to the first scan, to form a structure with the formation of a defined porosity, which may be regular or random. The scanned device may be programmed to proceed in a random generated manner to produce an irregular porous construct but with a defined level of porosity.

To produce a femoral component 10', the nature of the material formed as a result of laser melting of powder beads is principally dependent upon the thermal profile involved (heating rate, soaking time, cooling rate); the condition of the raw material (size and size distribution of powder particles); atmospheric conditions (reducing, inert or oxidizing chamber gas); and accurate control of the deposited layer thickness.

The apparatus for building such a component may include an Nd;YAG industrial laser, integrated to an RSG 1014 analog galvo-scanning head for providing a maximum scan speed of 500 mm per second. The laser beam is directed into an atmospherically-controlled chamber, which consists of two computer-controlled platforms with powder delivery and part building. The powder is delivered from a variable capacity chamber into the chamber and is transported by a roller to a build platform above a variable capacity build chamber.

In one embodiment, the build and delivery system parameters are optimized for an even 100 μm coating of powder to be deposited for every build layer. For implant manufacture, the metals chosen as surface materials are all difficult to process due to their affinity for oxygen. Titanium and other alloys are easily oxidized when processed by laser in oxygen-containing atmosphere, their oxide products have high melting points and poor flowability. For this reason, and to prevent the formation of other undesirable phases, the methods may be carried out under an Argon inert atmosphere in chamber. Pressure may remain at or below atmospheric pressure during the entire application.

The key laser parameters varied for forming the three-dimensional metallic porous structures are: (a) Laser scanning speed (v.) in (mms-1), which controls the rate at which the laser traverses the powder bed; (b) Laser power, P(W), which in conjunction with the laser spot size controls the intensity of the laser beam; and (c) Frequency, (Hz) or pulse repetition rate which controls the number of laser pulses per second. A lower frequency delivers a higher peak power and vice versa.

Although the structure has been discussed with regard to randomly depositing powder onto a substrate and selectively laser melting the powder while repeating layer after layer, in contrast, each layer or portion of a layer, may be scanned to create a portion of a plurality of predetermined unit cells. As successive layers of powder are deposited onto previous layers, the scanning and depositing of such layers continues the building process of a predetermined unit cell. When constructing the predetermined unit cells, the preferred embodiment includes employing a pulse high energy beam to form "spots" on the deposited powder layer. At least some of the "spots" are joined to produce struts or portions of struts, which constitute a portion of a predetermined unit cell. The spots may be created at random, in a continuous manner or a combination of the two. As disclosed herein, continuing the building process refers not only to a continuation of a unit cell from a previous layer but also a beginning of a new unit cell as well as the completion of a unit cell.

The invention can include a laser melting process that precludes the requirement for subsequent heat treatment of the structure, thereby preserving the initial mechanical properties of the core or base metal. The equipment used for the manufacture of such a device could be one of many currently available including the MCP Realizer, the EOSINT M270, Trumpf Trumaform 250, the Arcam EBM S12 and the like. The laser may also be a custom-produced laboratory device.

As successive layers of metal powder are deposited onto previous layers, a laser head projects a beam of energy onto locations of the powder to thereby form a spot or portion of a strut of a predetermined unit cell. The laser scans the powder bed and projects the energy beam based on the slice data of the model contained in the computer program.

After a layer has been completed, successive layers of metal powder may be deposited onto the previous layer by the use of a powder feeder. The powder feeder may work in conjunction with a piston that is lowered prior to the depositing of the additional layer of metal powder. The piston is desirably positioned under the substrate on which the metal structure is built. As each layer is processed, the piston may be lowered and an additional layer of metal powder deposited onto the previous layer. In this manner, each layer of unprocessed powder is positioned at the same distance from the laser head. The laser beam is capable of being directed along an X-Y coordinate system such that the desired location of the layer of metal powder can be engaged by the beam of energy. The guiding of the laser beam is dependent on the manufacturing system used. For example, if an e-beam system is employed the movement of the e-beam is controlled by deployment of the magnetic fields. If a laser beam apparatus is employed, the movement or guidance of the laser beam is controlled by a galvanometer.

The pore density, pore size and pore size distribution can be controlled from one location on the structure to another. It is important to note that successive powder layers can differ in porosity by varying factors used for laser scanning powder layers. Additionally, the porosity of successive layers of powder can be varied by either creating a specific type of predetermined unit cell or manipulating various dimensions of a given predetermined unit cell.

As described in U.S. patent application Ser. No. 11/027,421, such unit cell designs can be a tetrahedron, dodecahedron, octahedron, diamond, as well as many other various shapes. In addition, various struts may be removed from a unit cell to create an additional structure. Besides regular geometric shapes as discussed above, the unit cells of the present invention may be configured to have irregular shapes where various sides and dimensions have little if any repeating sequences. The unit cells can be configured to build constructs that closely mimic the structure of trabecular bone for instance. Unit cells can be space filling, in which all the space within a three-dimensional object is filled with cells, or interconnected where there may be some space left between cells but the cells are connected together by their edges. The unit cells can also be constructed in a form of a lattice. Additionally, adjacent lattices may be isolated from one another or only partially attached.

The unit cells can be distributed within the construct a number of ways. Firstly, they may be made into a block within a computer aided design ("CAD") system where the dimensions correspond to the extent of the solid geometry. This block can then be intersected with the geometry representing the component to produce a porous cellular representation of the geometry. Secondly, the cells may be deformed so as to drape over an object thus allowing the cells to follow the surface of the geometry. Thirdly, the cells can be populated through the geometry following the contours of any selected surface.

The unit cell can be open or complete at the surface of the construct to produce a desired effect. For instance, open cells with truncated lattice struts produce a surface with a porosity and impart the surface with some degree of barb, whereas closed cells can be "peaky" so as to increase surface roughness.

Modifying the lattice strut dimensions can control the mechanical strength of the unit cell. This modification can be in a number of key areas. The lattice strut can be adjusted by careful selection of build parameters or specifically by changing the design of the cross-section of each strut. The density of the lattice can similarly be adjusted by modification of the density of the unit cells as can the extent and shape of porosity or a combination thereof. Clearly the overall design of the unit cell will also have a significant effect on the structural performance of the lattice. For instance, dodecahedral unit cells have a different mechanical performance when compared to a tetrahedral (diamond) structure.

Thus, employing either of these methods or additional methods, the planar top side 50 of the femoral component 10' may be constructed including the porous pads 40', and the non-articulating internal surface 14' to a certain depth as required.

Further, as discussed in U.S. patent application Ser. No. 11/027,421, by utilizing the selective laser sintering process, the various constructs built may be formed having a particular arrangement such that various stress levels and pressure locations can be directed to a predetermined position. This allows the femoral component or other built component to mimic the characteristics of a human bone or joint.

Figure 3A:
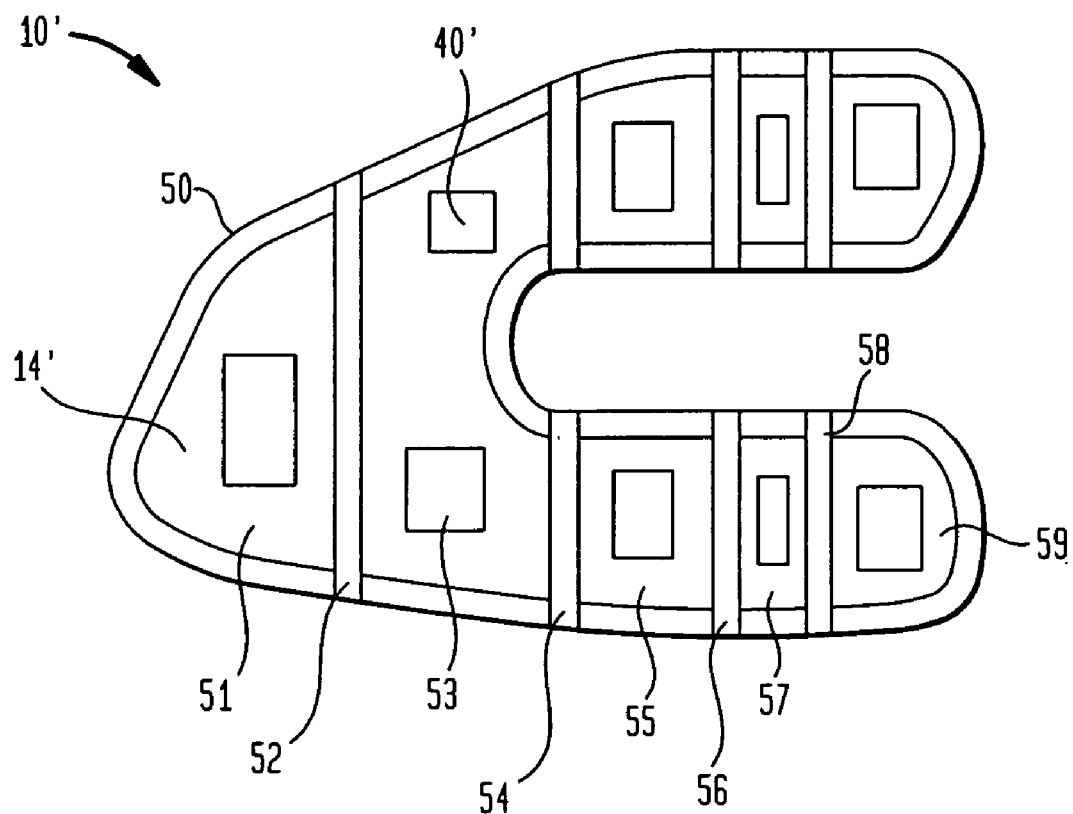
FIG. 3A is a top view of the embodiment of FIG. 2B at a later stage of the assembly process.
Figure 3B:
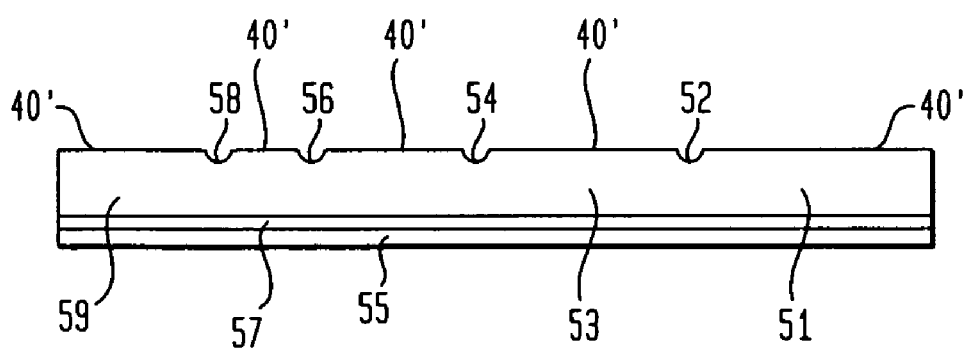
FIG. 3B is a side view of the embodiment of FIG. 3A.

As shown in FIGS. 3A and 3B, the planar top side 50 of femoral component 10' may be constructed with a plurality of grooves. In one such embodiment, a groove is positioned between various walls, chamfers and floors of the internal surface 14'. For example, a first groove 52 may be positioned between a first portion 51 and a second portion 53 of the planar top side 50; a second groove 54 may be positioned between the second portion 53 and a third portion 55 of the planar top side 50; a third groove 56 may be positioned between a third portion 55 and a fourth portion 57; while a fourth groove 58 is positioned between the fourth portion 57 and a fifth portion 59.

The various portions of the planar top side 50 correspond to the anterior wall 28, anterior chamfer 30, distal floor 32, posterior chamfer 34 and posterior wall 36, when looking at both the femoral component 10 and the planar top side 50 from left to right in FIGS. 1 and 3A. These corresponding structures and the way they relate to one another will be detailed below.

As previously discussed, the porous pads 40' may be constructed in tandem with the rest of the planar top side 50, such that the porous pads and planar top side 50 are a single element formed during the same stage in the process.

Figure 4A:
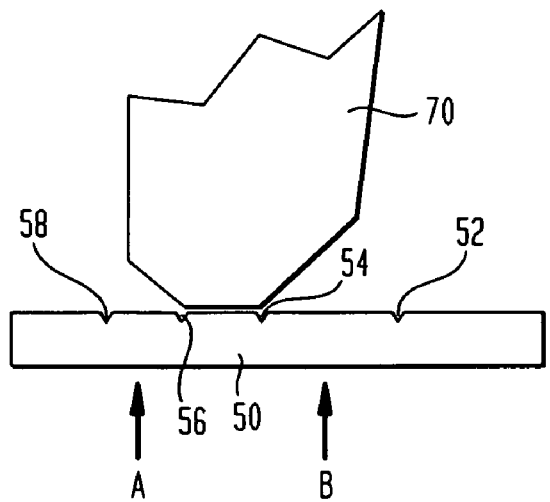
FIGS. 4A-4C is an illustration of one process according to the present invention.
Figure 4B:
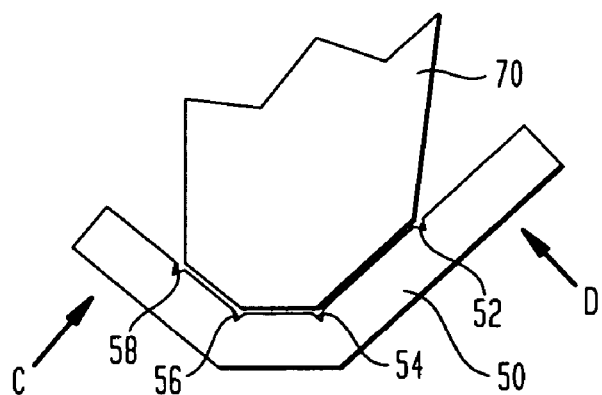
Figure 4C:
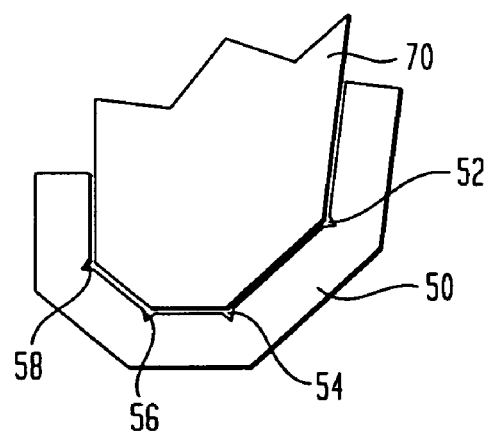

Once the planar top side 50 is removed from the building platform, it may be placed into a bending chamber (not shown in the figures). The bending chamber is able to apply pressure at specific locations on the planar top side 50 so as to bend and contort the planar top side 50 into a component that resembles the interior of the femoral component 10. The specific placements of the grooves, 52, 54, 56 and 58 as well as the specific locations where, how much, and for how long the pressure is applied can determine the final shape of the construct. In one bending operation, the planar top side 50 may be placed against a mandrel 70, as shown in FIG. 4A. The mandrel 70 has an outer surface that corresponds to the non-articulating internal surface 14 of the femoral component 10 and preferably has a shape that mimics a resected distal femur. Once the planar top side 50 is positioned correctly against the mandrel 70, a force in the directions of arrows A and B may be applied to the planar top side 50. As a result of the positioning of the grooves and the direction of the force applied, as shown in FIG. 4A, the planar top side 50 contorts and preferably assumes a shape similar to that illustrated in FIG. 4B. In one preferred embodiment, the forces in the direction of arrows A and B are specifically focused between grooves 56, 58 and 52, 54 respectively, thus enabling the planar top side 50 to bend at the desired locations, i.e., grooves 54 and 56. Of course, should the planar top side 50 begin to bend at an undesired location, the forces may be repositioned at different locations. Once the planar top side 50 has been shaped as shown in FIG. 4B, forces may be applied against the two exterior ends of the planar top side 50, as shown in FIG. 4B and denoted with arrows C and D. Preferably, the forces along the directions of C and D are applied to the outside of grooves 58 and 52 respectively. This preferably bends the planar top side 50 at grooves 58 and 52 about the mandrel 70, as shown in FIG. 4C. Once the planar top side 50 has been correctly shaped, it may be removed from engagement with the mandrel 70.

Figure 5:
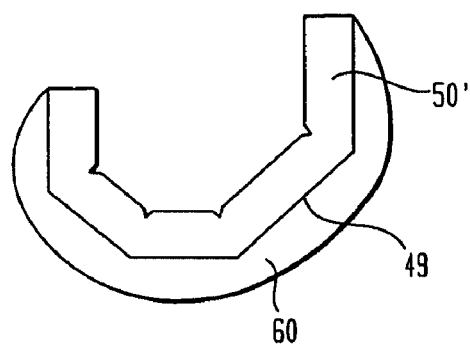
FIG. 5 is a side view of a final product according to the present invention.

The shaped planar top side 50' (FIGS. 5 and 6) having a shape and dimensions equivalent to an inner surface of a femoral component is removed from engagement with the mandrel 70. In order to complete the femoral component an articulating external surface may be applied. The articulating external surface can be finished in various ways. For instance, in one specific embodiment, a cold spray of a cobalt chrome alloy may be applied to the rear surface 49 of the shaped planar top side 50', as shown in FIG. 5. The cold spray may be preferred when the planar top side 50 is comprised of titanium.

During the cold spray process, the gaseous cobalt chrome alloy is deposited onto the rear surface 49 of the shaped planar top side 50', and as the gaseous cobalt chrome alloy solidifies, it forms the articulating external surface of the completed femoral component. The final surface may be machined by grinding and polishing the deposited cobalt chrome alloy such that the external surface 60 is able to articulate relative to a tibial component (not shown in the figures) once implanted during surgery. Although the cold spray process has been discussed with regard to employing a cobalt chrome alloy, various other materials may be employed such as but not limited to a high carbide chromium cobalt cermet ("C4"), or a titanium alloy. Choosing the material is dependent on various factors including the composition of the shaped planar top side 50' as well as the particular characteristics of the different material.

If a titanium alloy is used during the cold spray process, it may be necessary to apply a coating of a ceramic material. In such a process, the ceramic coating may be thermally sprayed onto the titanium alloy. The ceramic coating may then be grinded to a desired thickness. If necessary, the ceramic coating may be subjected to a heat treating process such as by vacuum sintering or a hot isostatic press (HIP) before a final grind and polish step.

Figure 6:
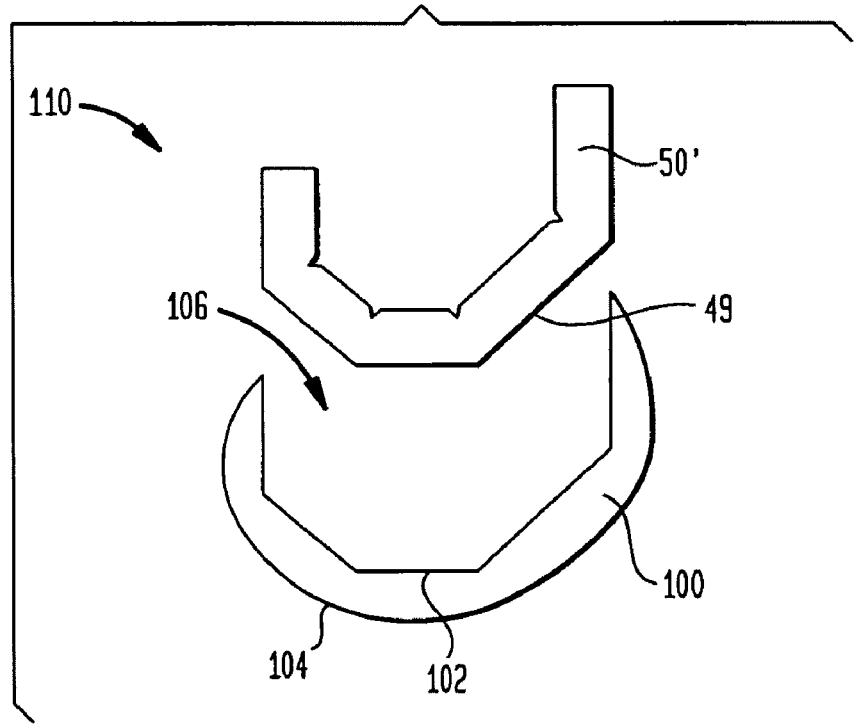
FIG. 6 is an exploded view of the embodiment in FIG. 5.

Rather than creating the articulating external surface 60 by cold spraying, it may be formed by sintering the shaped planar top side 50' to a forged or cast cobalt chrome femoral preform. The femoral preform is constructed during a separate process. The femoral preform 100, as shown in FIG. 6, includes an inner surface 102 and an outer surface 104. The inner surface 102 preferably has a contour that corresponds to the rear surface 49 of the shaped planar top side 50'. The outer surface 104 forms the articulating external surface of the final femoral component when assembled.

In order to complete the building process, the shaped planar top side 50' is received within a cavity 106 of the femoral component 100 such that the rear surface 49 of the shaped planar top side 50' abuts the inner surface 102 of the femoral preform 100. Once in position, the two components may be sinter bonded together using methods known to those skilled in the art to form a completed femoral component, similar to that formed using the cold spray process. As before, the final femoral component may be machined where required.

In an alternate embodiment, the femoral preform may be constructed utilizing selective laser sintering technology as opposed to casting or forging. During this process, a model of the preform may be inputted into a computer and relayed to the apparatus employed for building constructs. Based on the inputted model, actual three-dimensional models may be constructed, each having the same dimensions and shapes. Of course, the dimensions and shape of the inputted model can be refined and altered in order to change the dimensions and shape of the built models. As with the cold spraying process, the femoral preform may be constructed of other material such as but not limited to C4 or titanium alloy.

Besides forming the articulating surface of the final femoral component using a cold spray technique or sintering a femoral preform to the shaped planar top side 50', the articulating surface may be formed by hot spraying a cobalt chrome alloy, C4, titanium alloy or similar material onto the rear surface of the shaped planar top side 50' or employing a high energy laser powder deposition process also preferably using a cobalt chrome alloy, C4, titanium alloy or similar material. As before, if a titanium alloy is used, a ceramic coating may be required. In either case, the articulating surface of the femoral component is formed directly onto the shaped planar top side 50' to form a completed femoral component.

Figure 7:
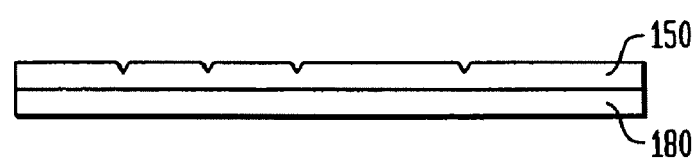
FIG. 7 is a side view of an embodiment at an early stage of a process.

In an alternate embodiment, the planar top side may be formed onto and attached to a thin flat plate. The plate is preferably comprised of a titanium alloy. When forming the planar top side with a thin flat plate, similar to the previous embodiment, a three-dimensional model of a femoral component such as that shown in FIG. 1 is inputted into a computer. The model is then "opened up" using computer software and a slice or plurality of slices of the model are reproduced using laser sintering technology as described above. In contrast to the embodiment described above, rather than building the planar top side of the digitized femoral component separately, the planar top side may be built onto and attached to a thin plate, as shown in FIG. 7. In a preferred embodiment as shown in FIG. 7, the planar top side 150 is directly built onto the thin plate 180 such that a single element is formed. The planar top side 150 may be thinner than the planar top side 50 such that when the planar top side 150 is built onto the plate 180, the combination of the two elements has a thickness equal to the thickness of the planar top side 50. Similar to the previous embodiment discussed above, the planar top side 150 and the plate 180 may be bent using a mandrel or other known techniques. Along this line, although not shown in the figures, the plate 180 may have various grooves and slots that aid in the bending process. As with planar top side 50, the combination of planar top side 150 and plate 180 may simply form the non-articulating internal surface of a femoral component. In order to complete the femoral component various techniques may be utilized against a rear surface of the plate 180, such as: a cold spray or hot spray of cobalt chrome alloy, C4, titanium, alloy or the like, sintering a forged femoral preform thereto, and high energy laser powder deposition of cobalt chrome alloy, C4, titanium or similar material using a laser or e-beam. In either of these embodiments, the final surface may be machined to achieve a finished articulating external surface of a completed femoral component.

In an alternate embodiment, as alluded to earlier, whether utilizing top planar side 50 or top planar side 150 in conjunction with thin plate 180, porous pads similar to those shown in FIG. 1 may be "grown" with the top planar sides 50 and 150. "Growing" the porous pads refers to building the porous pads' structures utilizing the laser technology discussed herein or alternate laser technology. A preferred embodiment includes "building" or "growing" the porous pads utilizing the predetermined unit cells discussed above. The porous pads may be added to the computer software used to digitize the femoral component such that during the building process the porous pads are made in tandem with the planar top sides 50 and 150. The porous pads can also be part of the original process, where they are scanned into a computer along with the original femoral component. With the introduction of the porous pads, either of planar top sides 50 or 150 may have additional grooves, slots and wedges that aid in the bending process. Also, the porous pads themselves may have various slots and openings to aid in the bending process.

Figure 8A:
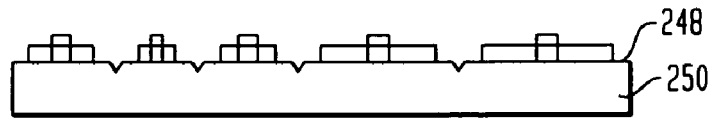
FIGS. 8A-8B are side views of alternate embodiments during various stages of an assembly process.
Figure 8B:
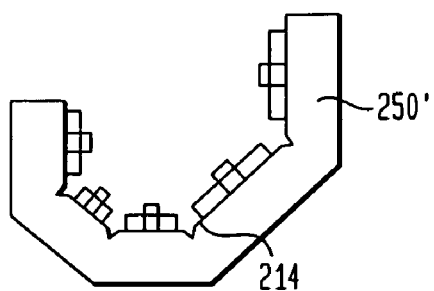

Although the porous pads have been discussed as being "grown" or "built" directly onto the non-articulating surface, i.e., the planar top side, of the femoral component, the porous pads can also be built separately and then attached to the non-articulating surface either before or after bending of the planar top sides 50 or 150. In such an embodiment, the planar top side may include locking mechanisms that enable an individual porous pad to be assembled and locked to the non-articulating internal surface of the femoral component. As before, the porous pads may be attached to the non-articulating internal surface prior to a bending process or after. In one such embodiment the non-articulating internal surface 214 or front surface 248 of planar top side 250 may include various clips 290 or extensions for locking the porous pads 240 to the surface, as shown in FIGS. 8A and 8B. In one preferred embodiment, the metallic porous pads are cooled, thereby causing them to shrink. The shrunken pads are then placed in position on the front surface 248 of the planar top side 250, as shown in FIG. 8A. The porous pads 248 are then heated, which causes them to expand while in place. The porous pads have dimensions that enable them to be fit loosely in position. However, when the porous pads expand because of heat or simply the reduction of the cooling, the pads have a dimension that forces the pads to tightly abut any borders, or locking elements designed to hold the pads in place. The expansion of the pads, along with the clips locks the porous pads in place. As shown in FIG. 8B, the planar top side 250 can be bent and formed into a shaped planar top side 250', similar to that discussed with reference to planar top side 50.

Figure 9:
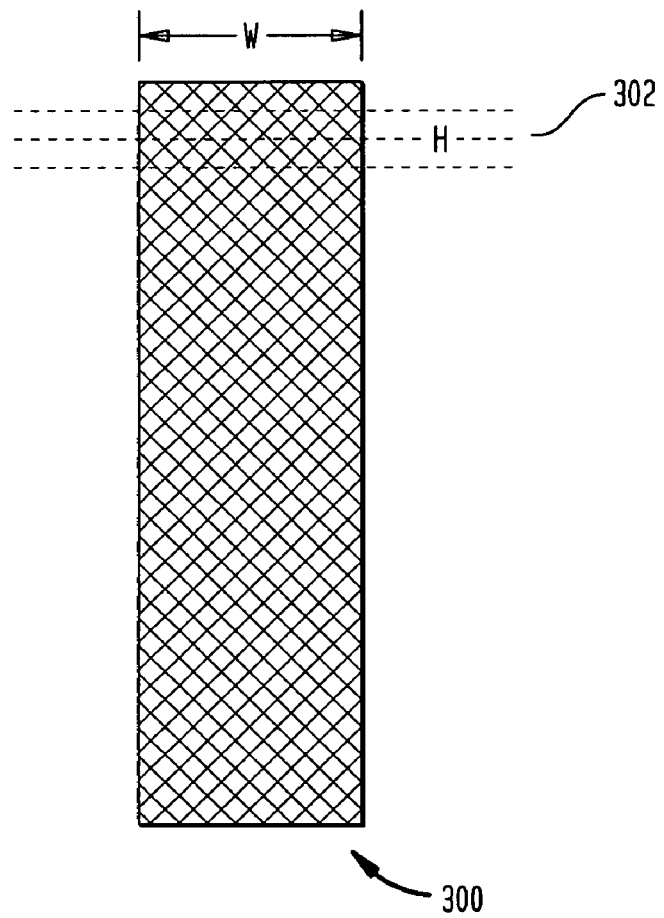
FIG. 9 is an illustration of one method of making a component used in conjunction with embodiments of the present invention.

The porous pads may be constructed individually, or in one preferred method a tall profile structure consisting of a plurality of porous pads may be constructed. For instance, as shown in FIG. 9, a tall construct 300 is built employing the selective laser sintering technology as discussed herein and preferably constructed using a plurality of predetermined unit cells. Although the construct 300 is shown as having a continuous porous gradient, the actual porous gradient may be varied from location to location along the construct 300. In one preferred embodiment, the construct 300 has a width W and a length L (into the page when looking at FIG. 9), that is substantially equal to the width W and height H of the porous pads.

The construct 300 may then be cut along dissection lines 302, only a few of which are shown. The dissection lines 302 preferably are placed at a distance equivalent to a desired height of the porous pads. Thus, as each cut is made along a dissection line 302, a completed porous pad is formed, which can then be assembled to a femoral component or other implant where bone ingrowth is desired. The construct 300 may be dissected or cut using a saw, laser or similar technology known to those in the art. The resultant porous pads may be laser sintered to the femoral component or other implant or simply assembled thereto using various clips and locking mechanisms.

Figure 10A:
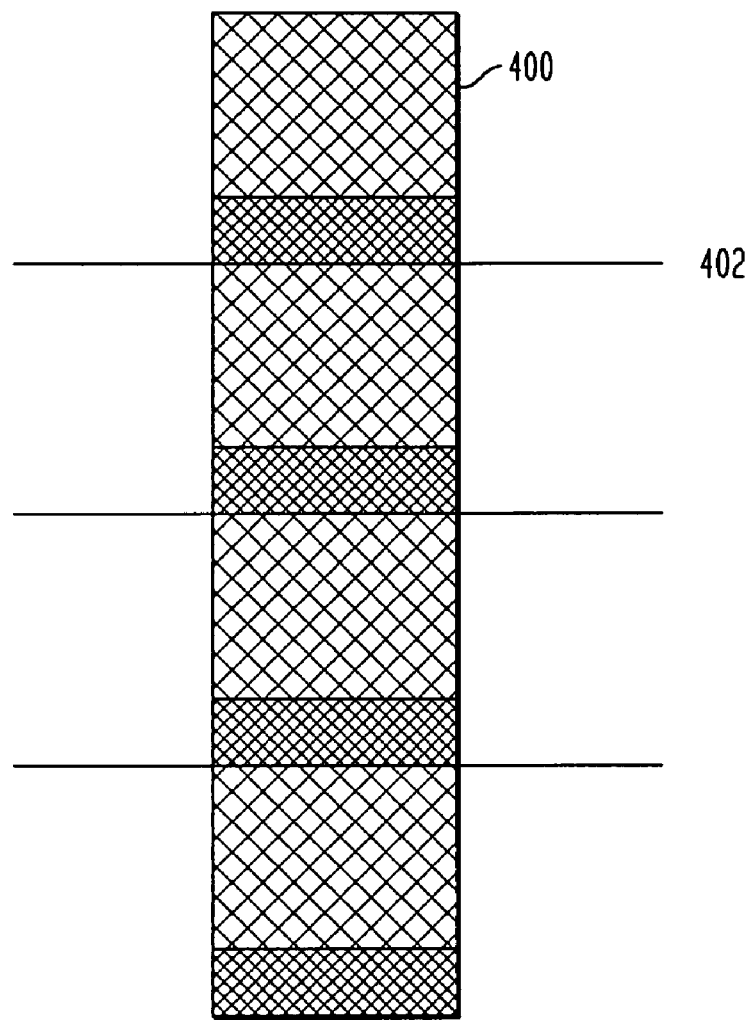
FIGS. 10A-10B are side views of alternate embodiments of the method illustrated in FIG. 9.
Figure 10B:
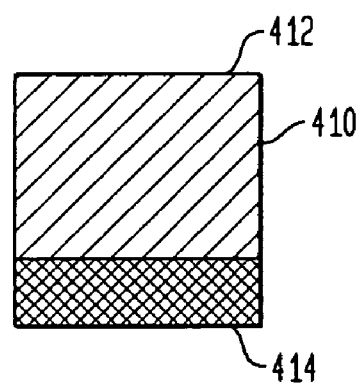

In an alternate embodiment, and as already alluded to, a construct 400 may be built having a varied porosity. In one preferred embodiment, as shown in FIG. 10A, the construct 400 has a porosity that decreases at a surface that will become the part of the porous pad that is attached to an additional component such as a femoral implant. Therefore, as shown in FIG. 10A, the construct 400 is preferably cut along dissection lines 402, such that a porous pad 410 is formed, as shown in FIG. 10B.

Porous pad 410 has a first surface 412 and a second surface 414. The second surface 414 is adapted to be placed against a surface of an implant, while the first surface 412 is adapted to confront bone and promote bone ingrowth. For this reason, the first surface 412 has a porosity specifically adapted for the promotion of bone ingrowth. The second surface 414 has a porosity that is less than the porosity of the first surface, thus providing a greater contact area between the porous pad 410 and the element to which the porous pad is attached to. This is particularly advantageous when the porous pad 410 is laser sintered to the implant.

Figure 11A:
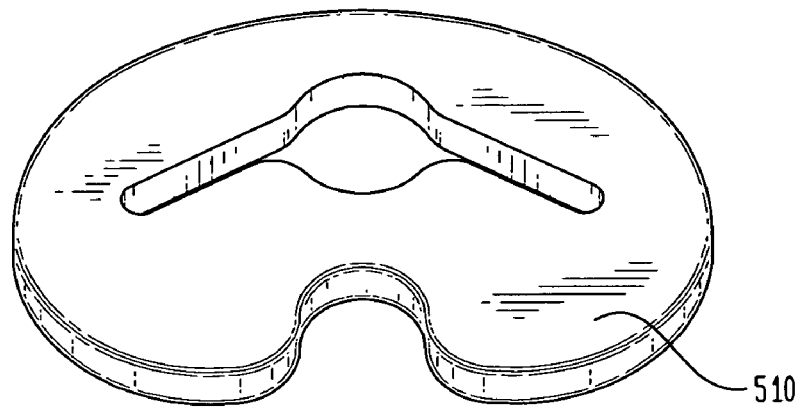
FIGS. 11A-11C are top perspective views of alternate embodiments of the present invention.
Figure 11B:
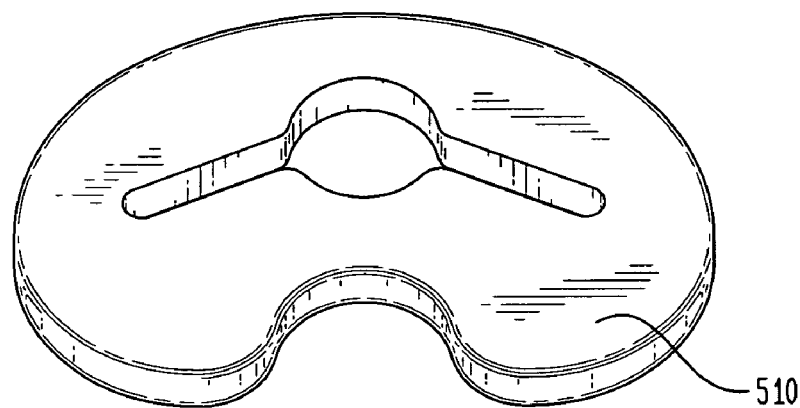
Figure 11C:
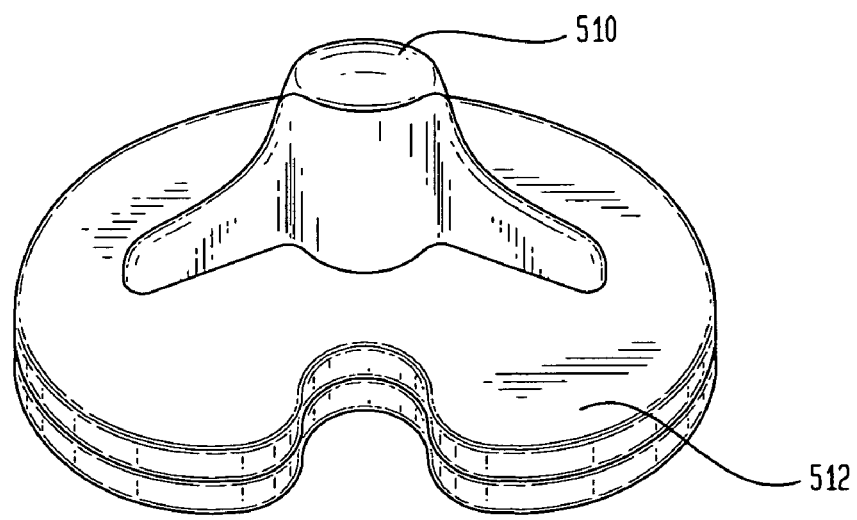

Although the constructs have been described and shown having a relatively symmetrical shape, the constructs can be built having various shapes and dimensions, as well as being adapted for mating to additional surgical implants. For instance as shown in FIGS. 11A-C, the construct may have a shape that once dissected produces pads 510 that are easily mountable to a tibial plateau 512. The pads may also be mounted to spinal implants, hip implants and most other implants where bone ingrowth is desired. In some embodiments, the porous pads may be positioned on an implant and then a further hand assembly of additional bone ingrowth promotional features may be attached thereto.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit or scope of the present invention as defined by the appended claims.

The invention claimed is:

1. A method of producing an orthopedic implant comprising the steps of:
   providing a flat open model having opposing first and second surfaces, wherein the flat open model has opposing first and second surfaces and at least one groove along the first surface;
   depositing at least a layer of powder on the first surface of the flat open model;
   building on at least a portion of the first surface of the flat open model using a high energy beam;
   applying a force to the flat open model at predetermined locations to thereby cause the flat open model to bend and assume a shape similar to a portion of an implant; and
   resurfacing the second surface of the bent flat open model by applying additional material such that the bent flat open model assumes the shape of a desired implant.

2. The method according to claim 1, wherein the portion of the implant is a portion of a femoral implant.

3. The method according to claim 2, wherein the first surface is an internal surface of a final product.

4. The method according to claim 3, wherein the at least one groove includes at least four positioned along the internal surface of the flat open model, wherein during the step of applying a force to the flat open model the force is applied in a direction from the second surface to the first surface such that as the flat open model bends it bends about the at least four grooves to form a U-like structure.

5. The method according to claim 4, wherein during the step of applying a force a mandrel is placed against the first surface of the flat open model.

6. The method according to claim 3, wherein prior to applying a force to the flat open model at least one porous pad is positioned between adjacent grooves on the first surface of the flat open model.

7. The method according to claim 6, wherein the at least one porous pad is integrally formed with the flat open model.

8. The method according to claim 6, wherein the at least one porous pad is a separate element mechanically secured to the flat open model.

9. The method according to claim 8, wherein prior to securing the at least one porous pad to the flat open model, the pad is cooled to thereby cause the pad to shrink in size, the pad is then placed between holding mechanisms disposed on the first surface of the open flat model, as the pad increases in temperature the pad increases in size causing the pad to become locked between the holding mechanisms.

10. The method according to claim 1, wherein the energy beam is a laser beam.

11. The method according to claim 1, wherein the energy beam is an e-beam.

* * * * *